United States Patent
Tokuda et al.

(10) Patent No.: US 8,461,374 B2
(45) Date of Patent: Jun. 11, 2013

(54) METHOD FOR PRODUCING HYDROXYALKYL (METH)ACRYLATE

(75) Inventors: Masanori Tokuda, Hatsukaichi (JP); Michiyuki Kouno, Otake (JP); Junichi Morioka, Otake (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 354 days.

(21) Appl. No.: 13/055,607

(22) PCT Filed: Aug. 28, 2009

(86) PCT No.: PCT/JP2009/004241
§ 371 (c)(1), (2), (4) Date: Jan. 24, 2011

(87) PCT Pub. No.: WO2010/023953
PCT Pub. Date: Mar. 4, 2010

(65) Prior Publication Data
US 2011/0124906 A1    May 26, 2011

(30) Foreign Application Priority Data

Aug. 28, 2008 (JP) ................. 2008-219548

(51) Int. Cl.
*C07C 67/26* (2006.01)

(52) U.S. Cl.
USPC ........................................ 560/209

(58) Field of Classification Search
None
See application file for complete search history.

(56) References Cited

U.S. PATENT DOCUMENTS 4,970,333 A * 11/1990 Rabon et al. ............... 560/209

FOREIGN PATENT DOCUMENTS

| JP | 10 330320 | 12/1998 |
|----|-----------|---------|
| JP | 2001 106653 | 4/2001 |

OTHER PUBLICATIONS

International Search Report issued Oct. 6, 2009 in PCT/JP09/004241 filed Aug. 28, 2009.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

Disclosed is a method for producing a hydroxyalkyl (meth) acrylate having high production efficiency and placing little burden on a production system. The method for producing a hydroxyalkyl (meth)acrylate comprises a reaction step of reacting (meth)acrylic acid with an alkylene oxide in a reactor while stirring a liquid containing (meth)acrylic acid and the alkylene oxide with a stirrer to obtain a reaction liquid containing a hydroxyalkyl (meth)acrylate, and thereafter a deaeration step of reducing a pressure in the reactor while stirring the reaction liquid with the stirrer to vaporize and remove an unreacted alkylene oxide in the reaction liquid, a number of stirring revolutions of the stirrer in the deaeration step being reduced to 30 to 85% of a number of stirring revolutions of the stirrer in the reaction step.

1 Claim, No Drawings

METHOD FOR PRODUCING HYDROXYALKYL (METH)ACRYLATE

TECHNICAL FIELD

The present invention relates to a method for producing a hydroxyalkyl (meth)acrylate.

The present application claims the priority of Japanese Patent Application No. 2008-219,548 filed on Aug. 28, 2008, the contents of which are incorporated herein by reference.

BACKGROUND ART

A method of reacting (meth)acrylic acid with an alkylene oxide is known as a method for producing a hydroxyalkyl (meth)acrylate. In this method, it is generally carried out to use an excess number of moles of alkyl ester as compared with a number of moles of (meth)acrylic acid.

Therefore, when (meth)acrylic acid is reacted with an alkylene oxide and thus a reaction liquid containing a hydroxyalkyl (meth)acrylate is obtained, an unreacted alkylene oxide is contained in the reaction liquid.

As a method for recovering the alkylene oxide in the reaction liquid, a method of reducing a pressure in a reactor to vaporize the alkylene oxide into gas in the reactor and then introducing the gas into an absorption tower to absorb the alkylene oxide in the gas into (meth)acrylic acid in the absorption tower is proposed (for example, Patent Document 1).

PRIOR ART REFERENCES

Patent Documents

Patent Document 1: Japanese Patent Application Laid-Open No. Hei 10-330,320

SUMMARY OF THE INVENTION

Problem to be Solved by the Invention

However, in the case where the pressure in the reactor is rapidly reduced, there occurs foaming of the reaction liquid and the foaming causes vibration of the reactor. Consequently, this places a burden on a production system in which the reactor is provided and thus troubles might occur. Whereas, in the case where the pressure in the reactor is slowly reduced, although the foaming is hard to occur, there causes a problem such that production efficiency becomes bad because it takes too long for the unreacted alkylene oxide to vaporize and at the same time by-products such as dialkylene glycol mono(meth)acrylate in which an alkylene oxide is further added to a hydroxyalkyl (meth)acrylate are produced because the unreacted alkylene oxide largely remains in the reactor. In particular, when a size of the reactor is large, the problem of the vibration of the reactor or the by-products becomes conspicuous.

The present invention provides a method for producing a hydroxyalkyl (meth)acrylate which places little burden on a production system, suppresses production of by-products, and has high production efficiency.

Means for Solving the Problem

The method for producing a hydroxyalkyl (meth)acrylate of the present invention is a method which comprises: a reaction step of reacting (meth)acrylic acid with an alkylene oxide in a reactor while stirring a liquid containing (meth)acrylic acid and the alkylene oxide with a stirrer to obtain a reaction liquid containing a hydroxyalkyl (meth)acrylate; and thereafter a deaeration step of reducing a pressure in the reactor while stirring the reaction liquid with the stirrer to vaporize and remove an unreacted alkylene oxide in the reaction liquid, a number of stirring revolutions of the stirrer in the deaeration step being reduced to 30 to 85% of a number of stirring revolutions of the stirrer in the reaction step.

Effect of the Invention

The method for producing a hydroxyalkyl (meth)acrylate of the present invention places little burden on a production system and has high production efficiency. In addition, the hydroxyalkyl (meth)acrylate to be obtained by the method of the present invention has a smaller amount of reaction by-products than in conventional methods.

BEST MODE FOR CARRYING OUT THE INVENTION

In the present invention, (meth)acrylic acid means acrylic acid or methacrylic acid.

(Reaction Step)

(Meth)acrylic acid and an alkylene oxide are reacted in a reactor while a liquid containing (meth)acrylic acid and the alkylene oxide is stirred with a stirrer, and the reaction liquid containing a hydroxyalkyl (meth)acrylate is obtained.

Examples of the alkylene oxide include ethylene oxide and propylene oxide, and ethylene oxide is preferable.

The amount of the alkylene oxide to be charged is preferably 1.0 to 1.2 moles relative to 1 mole of (meth)acrylic acid and particularly preferably 1.03 to 1.10 moles. When the amount of an alkylene oxide to be charged is 1.0 mole or more, (meth)acrylic acid which is difficult to separate from the product tends not to be mixed in the product, and thus there is a tendency such that purification of the product by a simple flush distillation becomes possible. When the amount of an alkylene oxide to be charged is 1.2 moles or less, productivity is improved because a recovery amount of an unreacted alkylene oxide becomes small.

It is preferable to use a catalyst for the reaction of (meth)acrylic acid with an alkylene oxide. Examples of the catalyst include various ammines, quaternary ammonium salts, trivalent iron compounds and co-catalysts, chromium compounds, silver or mercury, and metal (meth)acrylates. In addition, these catalysts can also be used in combination. The amount of the catalyst is preferably 0.01 to 10 parts by mass relative to 100 parts by mass of (meth)acrylic acid and more preferably 0.03 to 3 parts by mass. When the amount of the catalyst is 0.01 part by mass or more, the progress of the reaction tends to become fast. When the amount of the catalyst is 10 parts by mass or less, production of by-products tends to be suppressed and thus it is beneficial in the catalyst cost.

A polymerization inhibitor may be used in the reaction of (meth)acrylic acid with an alkylene oxide. Examples of the polymerization inhibitor include hydroquinone, hydroquinone monomethyl ether, catechol, phenothiazine, N, N-di-2-naphthyl-p-phenylenediamine, N-oxyl compounds, nitric acid, and nitrates. These polymerization inhibitors may be used alone or in a combination of two or more kinds thereof.

The amount of the polymerization inhibitor is preferably 0.01 to 1 part by mass relative to 100 parts by mass of (meth)acrylic acid. When the amount of the polymerization inhibitor is 0.01 part by mass or more, the effect of inhibiting polymerization tends to become good. When the amount of the polymerization inhibitor is 1 part by mass or less, separation of the polymerization inhibitor tends to become easy at the time of purification and thus the quality of the product becomes good and also the cost of the polymerization inhibitor is reduced.

The reaction temperature is usually 50 to 110° C. and preferably 60 to 90° C. When the reaction temperature is 50° C. or higher, the progress of the reaction tends to become fast, the conversion is improved, and the reaction tends to complete. When the reaction temperature is 110° C. or lower, occurrence of polymerization is suppressed and production of by-products is reduced.

The reaction may be carried out under any one of increased pressure, normal pressure, and reduced pressure. However, it is preferable to carry out the reaction under increased pressure in order to allow the alkylene oxide having a low boiling point to exist in a liquid state at the reaction temperature and thus to attain good contact between the alkylene oxide and (meth)acrylic acid.

Usually, the alkylene oxide is charged after (meth)acrylic acid, the catalyst, and the polymerization inhibitor have been charged in the reactor. The method for addition of the alkylene oxide can be one lump addition, continuous addition, or intermittent addition. In the case of the continuous addition, the charging rate may be raised and/or lowered in the middle. In the case where the reaction is not completed after the addition of the alkylene oxide, the reaction is continued, namely, what is called "aging" is carried out, until (meth)acrylic acid is consumed.

The reaction is usually continued until the concentration of (meth)acrylic acid in the reaction liquid becomes 1.0% by mass or less and preferably becomes 0.5% by mass or less so that mixing of (meth)acrylic acid in the product, which is difficult to separate, can be controlled at a small amount and thus purification of the product by a simple flush distillation can be carried out.

Note that, the concentration of methacrylic acid in the reaction liquid of 1.0% by mass corresponds to the conversion based on methacrylic acid of 98.5% by mass, and the concentration of acrylic acid in the reaction liquid of 1.0% by mass corresponds to the conversion based on acrylic acid of 98.2% by mass.

The reaction between (meth)acrylic acid and the alkylene oxide is carried out while the reaction system is stirred in order to remove heat and to make the temperature of the reaction system uniform because this reaction is an exothermic reaction. In addition, there is a tendency such that side reactions of the alkylene oxide added by dropping can be suppressed by the stirring and thus by the uniformity of the reaction system. The number of stirring revolutions in the reaction step may be suitably determined depending on a volume or characteristics of the reactor, a shape of the stirring blade, and presence or absence of a baffle plate. The number of stirring revolutions is industrially 10 to 300 rpm and preferably 30 to 200 rpm.

The number of stirring revolutions in the reaction step is not particularly limited as long as it is within the range in which heat removal can be carried out effectively or side reactions can be suppressed effectively, and it may be made constant or varied. For example, there may be difference in the number of stirring revolutions between the stirring during the dropping of the alkylene oxide and the stirring when aging is carried out after the dropping, or between other timings.

The number of stirring revolutions in the reaction step in the present invention means a constant value in the case where the reaction is carried out with the constant number of stirring revolutions, or means a number of stirring revolutions with which the stirring is carried out during the longest time in the reaction step in the case where the number of stirring revolutions is changed in the reaction step.

(Deaeration Step)

After the reaction is finished, the pressure in the reactor is reduced while the reaction liquid is stirred with the stirrer and an unreacted alkylene oxide in the reaction liquid is vaporized and removed.

After the reaction is finished, the inside of the reactor is under increased pressure owing to excess alkylene oxide, and it is preferable to reduce the pressure gradually and to remove the alkylene oxide at 10.7 kPa or less and more preferably at 2 kPa or less.

The temperature of the reaction liquid in the deaeration step is preferably 20 to 110° C. and more preferably 30 to 90° C. When the temperature of the reaction liquid is 20° C. or higher, the rate of removal of the alkylene oxide tends to become high. When the temperature of the reaction liquid is 110° C. or lower, production of by-products tends to be suppressed and polymerization tends to be suppressed.

In the present invention, the number of stirring revolutions of the stirrer in the deaeration step is reduced to 30 to 85% of that in the reaction step. When the number of stirring revolutions of the stirrer in the deaeration step is reduced to 85% or less of that in the reaction step, there is a tendency such that foaming of the reaction liquid becomes less likely to occur and thus vibration of the reactor can be suppressed even when the pressure inside the reactor is rapidly reduced. In addition, when the number of stirring revolutions of the stirrer in the deaeration step is 30% or more of that in the reaction step, there is a tendency such that bumping of the reaction liquid can be suppressed, and in the case when the reaction liquid is cooled during the deaeration step, cooling efficiency can be improved and thus production of by-products caused by reactions of the unreacted alkylene oxide can be suppressed.

The reduction of the number of stirring revolutions is preferably started just before the time when the pressure in the reactor is reduced and thus the unreacted alkylene oxide in the reaction liquid is vaporized.

The pressure in the reactor is gradually reduced in order to remove the unreacted alkylene oxide in the reaction liquid. Vibration of the reactor tends to occur when the pressure in the reactor reaches a high vacuum, and hence it is preferable to carry out the reduction of the number of stirring revolutions at this moment, and the number of stirring revolutions may be reduced gradually.

In the present invention, it is sufficient that the number of stirring revolutions of the stirrer in the deaeration step is once reduced to 30 to 85% of that in the reaction step, and the number of stirring revolutions of the stirrer may be raised again after the unreacted alkylene oxide has been removed to the extent that there has been no vibration of the reactor while the number of stirring revolutions has been reduced.

The alkylene oxide thus removed is subjected to a gas-liquid contact with (meth)acrylic acid, which is the other raw material of the synthesis of the hydroxyalkyl (meth)acrylate, at an absorption tower, and is recovered by absorption through contact with (meth)acrylic acid. Namely, when the target product is 2-hydroxyethyl acrylate, acrylic acid is used as an absorption liquid, and when the target product is 2-hydroxyethyl methacrylate, methacrylic acid is used as an absorption liquid.

An absorption tower is usually used for absorption through contact of the alkylene oxide. Examples of the type of the absorption tower include multistage and multitubular.

The temperature of (meth)acrylic acid as the absorption liquid may be a freezing point at the ambient pressure thereof or higher, and is preferably 20 to 50° C. When the temperature of the absorption liquid is 20° C. or higher, the absorption liquid does not freeze. When the temperature of the absorption liquid is 50° C. or lower, the rate of absorption of the alkylene oxide is improved.

The concentration of the alkylene oxide in the absorption tower is usually 1 mole or less relative to (meth)acrylic acid as the absorption liquid and preferably 0.005 to 0.1 mole. When the concentration of the alkylene oxide is 1 mole or less, there is a tendency such that the alkylene oxide can be sufficiently absorbed in the absorption liquid and thus a recovery rate of the alkylene oxide is improved.

(Meth)acrylic acid or the alkylene oxide is properly added to a thus obtained (meth)acrylic acid in which the alkylene oxide has been absorbed, and the resulting liquid is used as a raw material for the reaction of producing the hydroxyalkyl (meth)acrylate. The ratio of raw materials to be charged at this time is preferably 1.0 to 1.2 moles of the alkylene oxide relative to 1 mole of (meth)acrylic acid and particularly preferably 1.03 to 1.10 moles, as mentioned above.

In the method for producing the hydroxyalkyl (meth)acrylate of the present invention explained so far, foaming of the reaction liquid is less likely to occur even when the pressure inside the reactor is rapidly reduced at the time when the pressure in the reactor is reduced and the unreacted alkylene oxide in the reaction liquid is vaporized and removed because the number of stirring revolutions of the stirrer in the deaeration step is reduced to 30 to 85% of that in the reaction step. As a result, burden on a production system becomes small. In addition, production efficiency is good because the inside of the reactor can be rapidly reduced. The lower limit of the number of stirring revolutions of the stirrer in the deaeration step is preferably reduced 50% or more of that in the reaction step and more preferably reduced 60% or more. The upper limit of the number of stirring revolutions of the stirrer in the deaeration step is preferably reduced 80% or less of that in the reaction step.

The present invention realizes the effect thereof more, as the size of the reactor becomes larger, and it is preferable to use the reactor having the size of 1,000 to 30,000 L because the effect is remarkable.

EXAMPLES

Hereinafter, Examples will be shown.

Example 1

(Reaction Step)

To a high-pressure reaction vessel equipped with a stirrer, 430.45 parts by mass of methacrylic acid as a raw material, 3.44 parts by mass of iron methacrylate as a catalyst, and 0.117 part by mass of sodium nitrite as a polymerization inhibitor were charged, and the temperature of the resulting liquid was raised to the reaction temperature of 60° C. To the above liquid, 255.49 parts of ethylene oxide were dropped over a period of 2 hours while the liquid was stirred at a number of stirring revolutions of 110 rpm, and after the dropping was finished, the resulting liquid containing methacrylic acid and ethylene oxide was maintained at 60° C. for 6 hours while being stirred at a number of stirring revolutions of 110 rpm.

(Deaeration Step)

After the reaction was finished, the number of stirring revolutions of the stirrer was reduced to 82 rpm (which is 75% of the number of stirring revolutions in the reaction step) and ethylene oxide contained in the reaction liquid was vaporized while the reaction liquid was stirred at the same rate. After the pressure of the reaction vessel became a normal pressure, the inside of the reaction vessel was decompressed with a vacuum generation device and the gas inside the reaction vessel was evacuated.

The deaeration step was finished when the pressure to be measured with a pressure gauge provided inside the reaction vessel became 2 kPa, and the vacuum generation device was stopped.

Foaming of the reaction liquid, which could cause vibration of the reaction vessel, was not observed during the deaeration step. In addition, 4.17 parts by mass of diethylene glycol monomethacrylate was contained in 2-hydroxyethyl methacrylate obtained.

Example 2

The same procedure as in Example 1 was carried out except that the number of stirring revolutions of the stirrer in the deaeration step was changed to 91 rpm (which is 83% of the number of stirring revolutions in the reaction step), and 2-hydroxyethyl methacrylate was produced.

Foaming of the reaction liquid, which could cause vibration of the reaction vessel, was not observed during the deaeration step. In addition, 4.13 parts by mass of diethylene glycol monomethacrylate was contained in 2-hydroxyethyl methacrylate obtained.

Example 3

The same procedure as in Example 1 was carried out except that the number of stirring revolutions of the stirrer in the deaeration step was changed to 36 rpm (which is 33% of the number of stirring revolutions in the reaction step), and 2-hydroxyethyl methacrylate was produced.

Foaming of the reaction liquid, which could cause vibration of the reaction vessel, was not observed during the deaeration step. In addition, bumping of the reaction liquid was not observed.

Comparative Example 1

The same procedure as in Example 1 was carried out except that the number of stirring revolutions of the stirrer in the deaeration step was changed to 110 rpm (which is the same as the number of stirring revolutions in the reaction step), and 2-hydroxyethyl methacrylate was produced.

Foaming of the reaction liquid, which caused vibration of the reaction vessel, was observed during the deaeration step. In addition, 4.08 parts by mass of diethylene glycol monomethacrylate was contained in 2-hydroxyethyl methacrylate obtained.

INDUSTRIAL APPLICABILITY

The production method of the present invention is useful for production of a hydroxyalkyl (meth)acrylate.

What is claimed is:

1. A method for producing a hydroxyalkyl (meth)acrylate, comprising:
  a reaction step of reacting (meth)acrylic acid with an alkylene oxide in a reactor while stirring a liquid containing (meth)acrylic acid and the alkylene oxide with a stirrer to obtain a reaction liquid containing a hydroxyalkyl (meth)acrylate; and thereafter a deaeration step of reducing a pressure in the reactor while stirring the reaction liquid with the stirrer to vaporize and remove an unreacted alkylene oxide in the reaction liquid, a number of stirring revolutions of the stirrer in the deaeration step being reduced to 30 to 85% of a number of stirring revolutions of the stirrer in the reaction step.

* * * * *